July 3, 1956 C. D. CORLISS Plant Pat. 1,492
AJUGA REPTANS PLANT
Filed Aug. 2, 1955
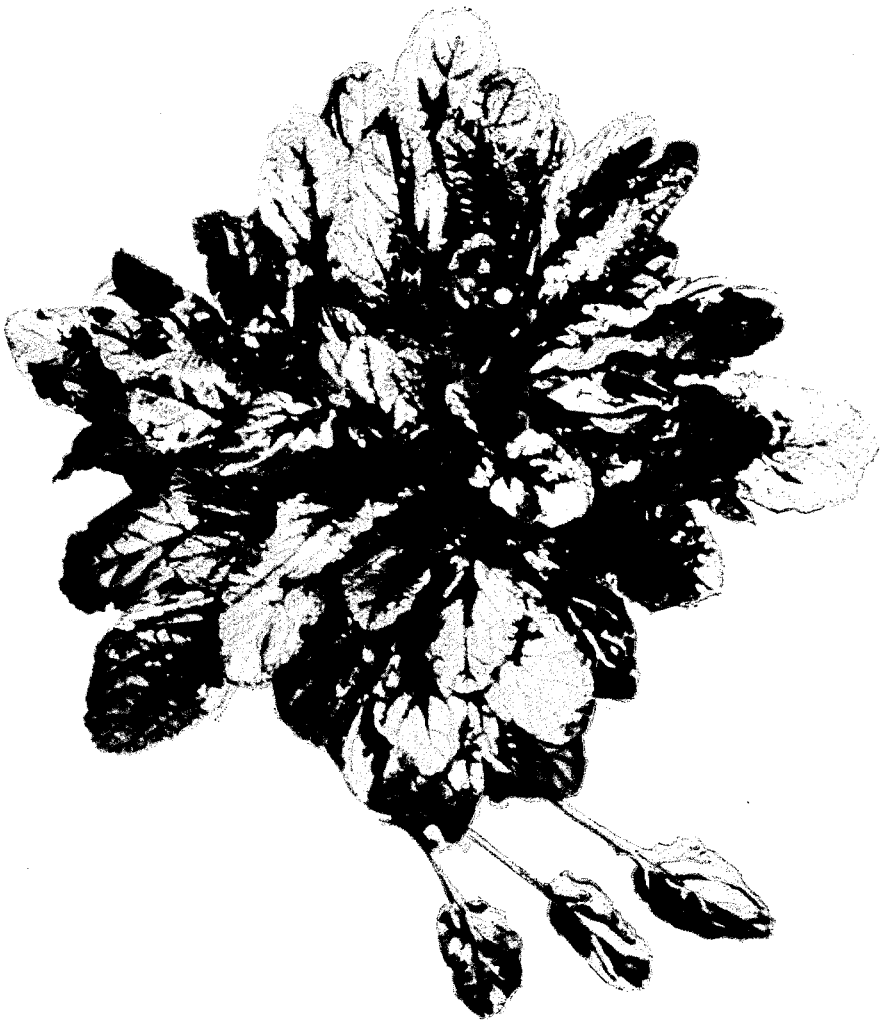
INVENTOR
Clifford D Corliss
By Orville M. Kile
PLANT PATENT AGENT United States Patent Office Plant Pat. 1,492
Patented July 3, 1956

1,492

AJUGA REPTANS PLANT

Clifford D. Corliss, Gloucester, Mass., assignor to Corliss Bros., Inc., Gloucester, Mass., a corporation of Massachusetts Application August 2, 1955, Serial No. 526,091

1 Claim. (Cl. 47—60)

My present discovery relates to a distinct variety of *Ajuga reptans* plant and is a distinct improvement over the presently known varieties of the *Ajuga reptans*. The variety originated as a seedling from *Ajuga reptans* Multicolor (unpatented), discovered by me in the nurseries in Massachusetts of which I am part owner.

I asexually reproduced this plant and since the original reproduction large numbers of plants of the new variety have been asexually reproduced at our nurseries in Massachusetts by means of division, cuttings and stolons, with the result that the variety appears to have characteristics that are firmly fixed.

Outstanding features of my new variety are the vigorous growth, producing a neatly rounded perennial plant, and the distinctive coloring of its foliage—the summer and fall coloring of which is rich and striking. It is highly ornamental and is desirable as a bedding and ground cover plant.

The accompanying illustration is a hand-colored photograph and shows a specimen of my variety of Ajuga plant, as viewed from the top, and with three separate leaves distinctly showing. It depicts a typical plant in approximately its natural colors and position on the leafblade, which distinguish the new variety from its parent and other known varieties, as they appear in the mid-summer.

In the following detailed description of the plant, the usual dictionary means of the color nomenclature is intended.

THE PLANT

Growth: Rugged and robust. Acaulescent; very hardy; dense spreading; low, attaining a height of 10 to 15 cms.; creeping by short stolons, forming mats.

Disease and pest resistance: Since the time of my discovery of the original plant, this variety has had no diseases or pest troubles.

Foliage:

*Size.*—Length of average leaf approximately 15 cms.; width, approximately 5 cms.

*Shape.*—Spatulate or obovate, narrowed to margined petioles. Apex of some leaves retuse. Edges irregularly undulate-sinuate, with indications of crenation.

*Arrangement.*—Arranged in a basal cluster.

*Texture and aspect.*—Rugose; coriaceous; shiny puberulent.

*Petioles.*—Margined; length varies from sub-sessile to 7 cms.

*Color.*—The early spring leaves are dark green. In late June or early July they start to change to the metallic purplish-red and at the same time the blotches of various colors become more prominent. As the season progresses, the color of the leaves and blotches are more variable until fall, at which times the leaves are the dark metallic-bronzy-red. Variations or markings on the leaf blades are irregular and blotchy—some reaching the margin, and a few marginal. Colors of blotches are quite variable—some ranging from almost white, through cream, pale yellow and pale green, while others range from very pale pink, through dark pink, brick red and even bronze, with sometimes a mixture.

Flowers:

*Season.*—Bloom May to July.

*Size.*—Small.

*Color.*—Dark blue.

*Form.*—Labiate.

*Arrangement.*—In whorls on short spikes. Corolla exserted.

*Calyx.*—Not yoked; five-lobed; green; sparsely pubescent.

Petals:

*Shape.*—Labiate, with short upper lip. Large spreading lower lip with middle lobe emarginate; 2-cleft.

*Color.*—Dark blue.

COMPARISON

My new variety resembles its parent, *Ajuga reptans* Multicolor, more than any other variety known to me, but greatly differs from that variety, principally as follows:

In the variety Multicolor the leaves are mostly medium green but occasionally spotted with yellow, brown or red, which variations in color of the leaves are primarily marginal.

In my new variety, the foliage coloring is more varied and more blotchy, the markings are more strongly pronounced on the central portion of the leaf blades and much less confined to the margins. The colors of the blotches of my variety are much more varied, vivid and brilliant than those in the variety Multicolor.

Having thus disclosed my discovery, I claim:

The new and distinct variety of *Ajuga reptans* plant, substantially as herein shown and described, characterized particularly by the low-growing habit and tendency to form low, dense mats; its vigorous growth; its production of a neatly rounded plant; and the distinctive, brilliant, varied and pleasing coloring of its leaves as described.

No references cited.